(12) United States Patent
Robbins

(10) Patent No.: US 10,549,086 B2
(45) Date of Patent: Feb. 4, 2020

(54) CIRCUMFERENTIAL MULTI-DEFIBRILLATOR, MULTI-AXIS ELECTRODE PAD BAND

(71) Applicant: Vincent D. Robbins, Hamilton Square, NJ (US)

(72) Inventor: Vincent D. Robbins, Hamilton Square, NJ (US)

( * ) Notice: Subject to any disclaimer, the term of this patent is extended or adjusted under 35 U.S.C. 154(b) by 156 days.

(21) Appl. No.: 15/386,130

(22) Filed: Dec. 21, 2016

(65) Prior Publication Data

US 2017/0232248 A1    Aug. 17, 2017

Related U.S. Application Data

(60) Provisional application No. 62/270,200, filed on Dec. 21, 2015.

(51) Int. Cl.
*A61N 1/39*    (2006.01)
*A61N 1/04*    (2006.01)

(52) U.S. Cl.
CPC ........... *A61N 1/046* (2013.01); *A61N 1/0476* (2013.01)

(58) Field of Classification Search
CPC ................. A61N 1/0484; A61B 5/04085
See application file for complete search history.

(56) References Cited

U.S. PATENT DOCUMENTS

| 4,121,575 | A | 10/1978 | Mills et al. |
| 5,184,620 | A | 2/1993 | Cudahy et al. |
| 5,341,806 | A * | 8/1994 | Gadsby .............. A61B 5/04085 600/391 |
| 5,383,840 | A * | 1/1995 | Heilman ............. A61M 1/1068 600/17 |
| 5,466,244 | A | 11/1995 | Morgan |
| 5,558,617 | A | 9/1996 | Heilman et al. |
| 5,785,040 | A | 7/1998 | Axelgaard |
| 6,065,154 | A * | 5/2000 | Hulings ............... A61N 1/0484 2/102 |
| 8,626,260 | B2 | 1/2014 | Crosby |
| 2003/0216787 | A1 * | 11/2003 | Worden ............... A61N 1/3918 607/5 |
| 2014/0039595 | A1 * | 2/2014 | Kroll-Orywahl ....... A61F 5/028 607/149 |
| 2014/0073895 | A1 | 3/2014 | Freeman et al. |

OTHER PUBLICATIONS

Novelty Search Report, Application No. 62270200, dated Nov. 9, 2015, 18 pages.

* cited by examiner

*Primary Examiner* — Michael J D Abreu

(74) *Attorney, Agent, or Firm* — Ziegler IP Law Group, LLC

(57) ABSTRACT

A multi-axis defibrillator electrode band includes a stretchable band having a first end and a second end; and at least one pair of defibrillation electrodes embedded in the stretchable band between the first end and the second end, wherein a first electrode in the electrode pair is disposed opposite a second electrode in the electrode pair to define a conduction channel from the first electrode to the second electrode when the band is in a usage position for a defibrillation event.

16 Claims, 3 Drawing Sheets

CIRCUMFERENTIAL MULTI-DEFIBRILLATOR, MULTI-AXIS ELECTRODE PAD BAND

CROSS-REFERENCE TO RELATED APPLICATIONS

This application claims priority to, and the benefit of, U.S. Provisional Patent Application Ser. No. 62/270,200, filed on 21 Dec. 2015, the disclosure of which is incorporated herein by reference in its entirety.

BACKGROUND

The present disclosure generally relates to defibrillator electrodes and pads, and in more particularly to a multi-axis defibrillator electrode pad band.

Recent medical research indicates that, for patients who need defibrillation, more than one defibrillation provided simultaneously, or as close to simultaneously as possible, would produce better patient survival outcomes for some individuals, rather than traditional single defibrillations. In addition, there is suspicion among some leading emergency medical physicians and cardiologists that simultaneously provided defibrillations along various or multiple axis through the heart would produce even better patient outcomes for those with lethal cardiac rhythms.

In multi-axis defibrillation, a number of defibrillator pads are used. The different defibrillator pads must be placed in specific locations on and around the chest or thorax of the patient, to ensure that an electrical discharge passes through the area of the heart. The defibrillator pads will be electrically coupled to the defibrillator and must be organized in pairs. Generally, each defibrillator pad will be coupled to a wire that is connected to the defibrillator. In a situation where there is a plurality of defibrillator pads, there will be a plurality of electrical connections to the defibrillator. Ensuring that the plurality of pads are properly paired and connected can be confusing. This can be especially problematic in environments and settings such as an emergency room or in the field. In these types of settings, there can be a number of activities going on at once, in less than ideal conditions, producing a seemingly busy or chaotic situation. In such less than ideal settings, it can take more time to organize and apply multiple EKG and defibrillation electrodes and pads.

Accordingly, it would be desirable to provide an electrode pad system that addresses at least some of the problems identified above.

SUMMARY

The aspects of the disclosed embodiments are directed to a multi-axis electrode band assembly. In one embodiment the multi-axis electrode band assembly includes a stretchable band having a first end and a second end; and at least one pair of defibrillation electrodes embedded in the stretchable band between the first end and the second end, wherein a first electrode in the electrode pair is disposed opposite a second electrode in the electrode pair to define a conduction channel when the band is in a usage position for a defibrillation event.

In another aspect, the aspects of the disclosed embodiments are directed to a multi-axis defibrillator electrode band for use in a multi-axis defibrillation of a person during a cardiac event. In one embodiment, the multi-axis defibrillator electrode band includes a stretchable band, the stretchable band comprising a plurality of defibrillation electrodes, wherein each electrode of the plurality of electrodes has a relative pre-defined position on the stretchable band and a relative spacing from an adjacent electrode; and wherein in an expanded state of the stretchable band, the relative spacing between adjacent electrodes is maintained.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the following detailed portion of the present disclosure, the aspects of the disclosed embodiments will be explained in more detail with reference to the example embodiments shown in the drawings, in which.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and unless otherwise indicated, they are merely intended to conceptually illustrate the structures and procedures described herein. In addition, any suitable size, shape or type of elements or materials could be used.

BRIEF DESCRIPTION OF THE DISCLOSED EMBODIMENTS

As described herein, the exemplary embodiments overcome one or more of the above or other disadvantages known in the art.

Figure 1:
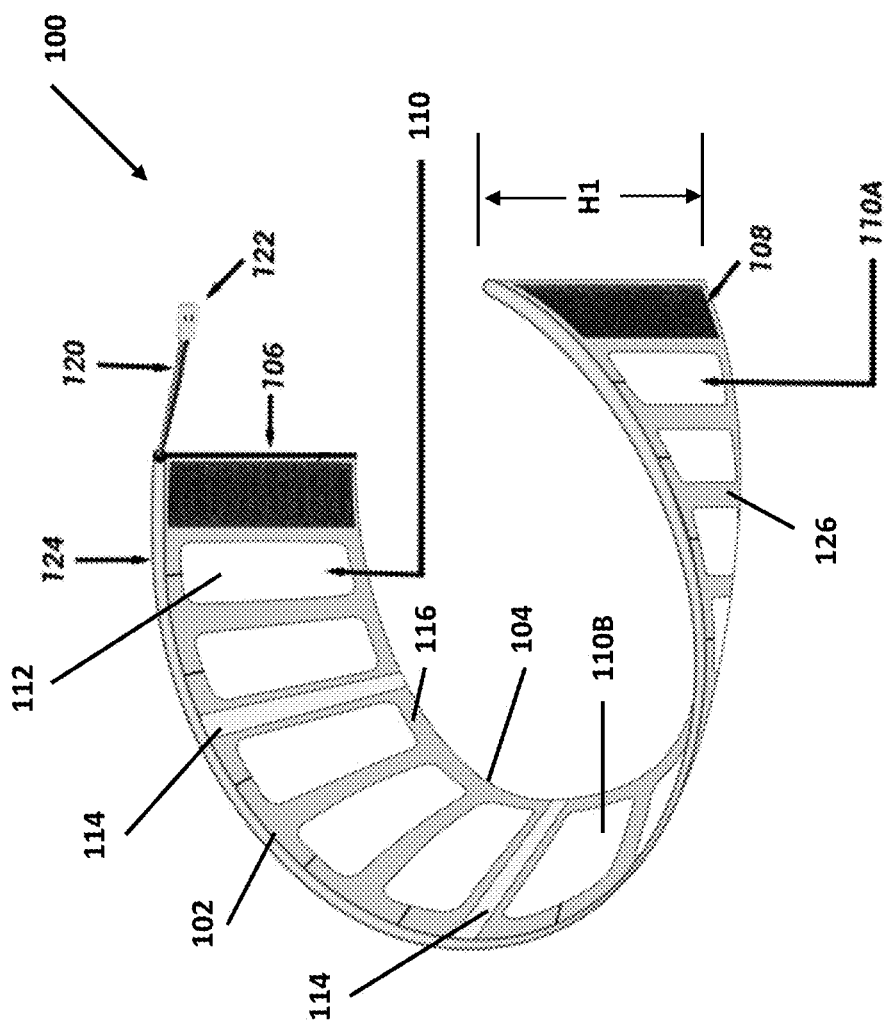
FIG. 1 is a perspective view of an exemplary electrode band incorporating aspects of the disclosed embodiments.
Figure 2:
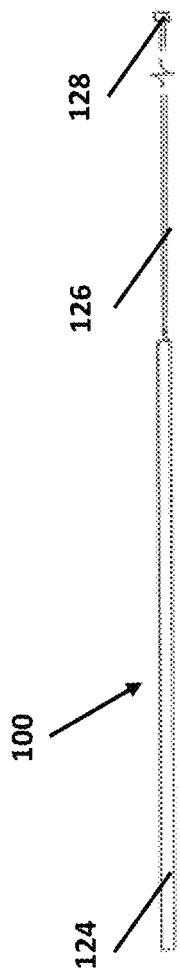
FIG. 2 is a top view of the exemplary electrode band incorporating aspects of the disclosed embodiments.

Referring to FIG. 1, the aspects of the disclosed embodiments provide a multi axis electrode band assembly 100, generally referred to herein as an electrode band. The aspects of the disclosed embodiments are generally configured to provide an electrode assembly for multi axis defibrillation that allows the plurality of electrodes to be maintained in a pre-configured arrangement prior to use as well as enable the electrodes to be reliably placed in the required positions on the body of patient.

In the example shown in FIG. 1, the electrode band 100 includes a plurality of defibrillator pads or electrodes 110. The electrodes 110 are configured for defibrillation, as is generally understood. The electrodes 110 are suitably disposed on or embedded in the band 100. One example of suitable electrodes are Covidien Kendall #1310P Multi-Function Defibrillator Electrodes.

In one embodiment, the electrodes 110 will generally include a conductive gel on one side 112 of the electrode 110, generally referred to as the patient side of the band 100. For example, the surface or side 112 of each electrode 110 that comes in contact with the patient's thorax or chest, would be coated with a stable, non-liquid, semi solidified gel that would be capable of conducting electricity (defibrillator discharges) efficiently. The gel would not migrate away from the surface 112 of the electrode 110. The electrodes 110 will be separated by enough space, and the size of the gel coating would be contained within the perimeter of the electrode 110 sufficiently, to prohibit electricity discharges from being conducted to adjacent electrodes or pads.

In one embodiment, the electrode pads 110 are paired to form electrode pad pairs. Typically, one electrode, such as electrode 110A is "paired" with an electrode, such as electrode 110B on a substantially "opposite" side of the band 100 when the band 100 is properly positioned around the chest of the patient. In the example of FIG. 1, electrodes 110A and 110B form an electrode pair. An electrode pair, such as electrode pads 110A, 110B, is configured to create an electrical pathway for the electrical current, or "electric shock" that is delivered by a defibrillator during a defibrillation event. The electrical pathway is through the body of the patient, and in particular the heart. Although only one electrode pair 110A, 110B is referenced, the electrode band 100 can include any suitable number of electrode pairs, each defining an anterior-posterior electrical conduction pathway. As will be described further herein, the electrode band 100 of the disclosed embodiments is configured to encircle the chest of a patient, with the different electrode pairs positioned at different anterior-posterior locations for multi-axis defibrillation.

For example, a typical electrode band 100 of the disclosed embodiments might include three to five electrode pairs (six to ten electrodes), depending on the desired number of electrical pathways for a defibrillation event. The electrode band 100 of the disclosed embodiments can be configured for any suitable number of electrode pairs. For example, the number of electrode pairs in an electrode band can be dependent upon a size of a patient. In one embodiment, the electrode band 100 can be configured as small medium and large. A small band 100 may include two to four pairs or electrodes, a medium band six to ten electrode pairs, while a large band has 12-14 electrode pairs. The number of pairs described herein and the exemplary band 100 of the disclosed embodiments can be configured for any sized patient and can include any number of pairs of electrodes.

The electrode band 100 is configured to be placed on and encircle most or all of the chest portion of a patient, also referred to herein as the thorax. The electrode band generally comprises an elastic and stretchable material suitable for use with defibrillator electrodes. One example of a suitable material for the electrode band 100 is COTOWIN® 6-inch Wide White Knit Heavy Stretch High Elasticity Elastic Band composed of 85% polyester, 15% rubber.

Figure 5:
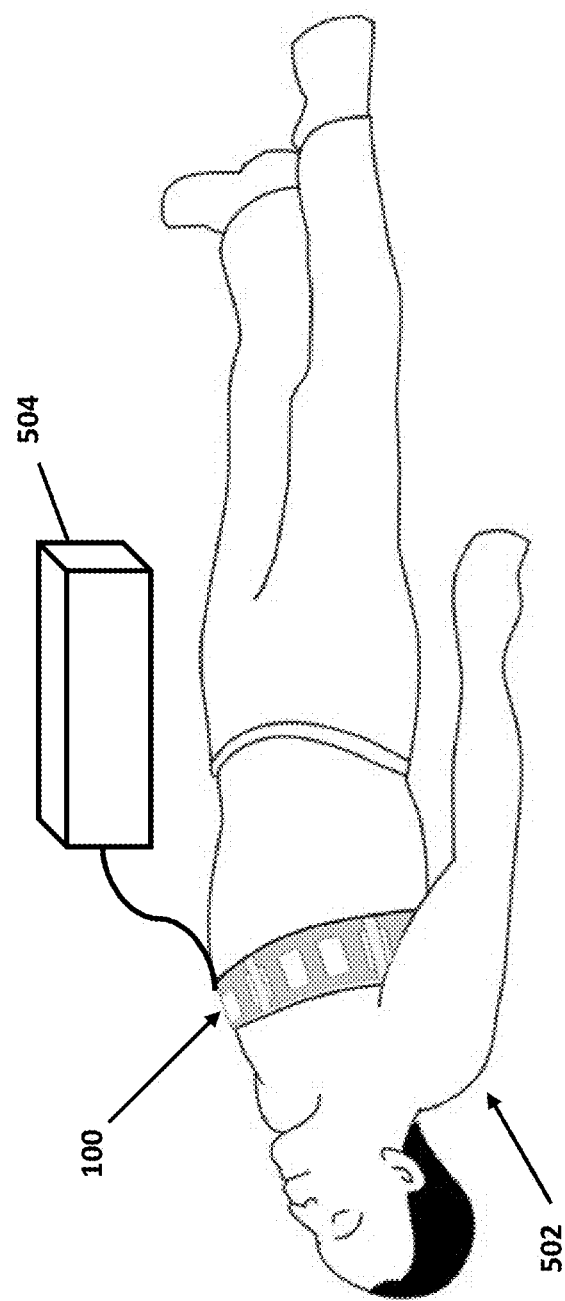
FIG. 5 illustrates an exemplary application of the electrode band incorporating aspects of the disclosed embodiments.

FIG. 5 illustrates an exemplary application of the electrode band assembly 100 to a patient 502. Generally, the exemplary application of the electrode band 100 is in the case of a patient that is suspected of potentially worsening into, a lethal cardiac arrhythmia that could require defibrillation as a treatment modality. With an appropriately designed multi-axis defibrillator 504 attached, this electrode band 100 would allow selective levels of electrical output to be discharged through the electrodes 110, and in particular selected ones of the electrode pairs 110A, 110B, or combinations of electrode pairs. The electrodes 110 in each electrode pair 110A, 110B are generally located anteriorly/posteriorly opposite each other on the thorax. The aspects of the disclosed embodiments enable the relative anterior/posterior positioning of the electrode pairs 110A, 110B in the electrode band 100 to be maintained for any size of patient.

Figure 3:
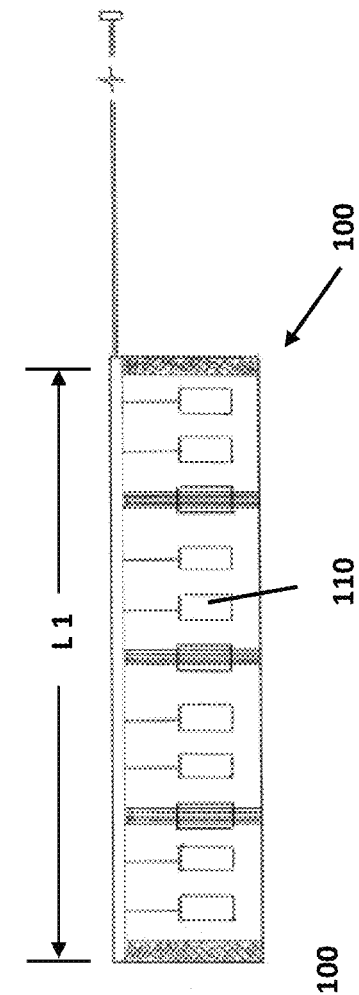
FIG. 3 is an end view of the exemplary electrode band incorporating aspects of the disclosed embodiments.
Figure 4:
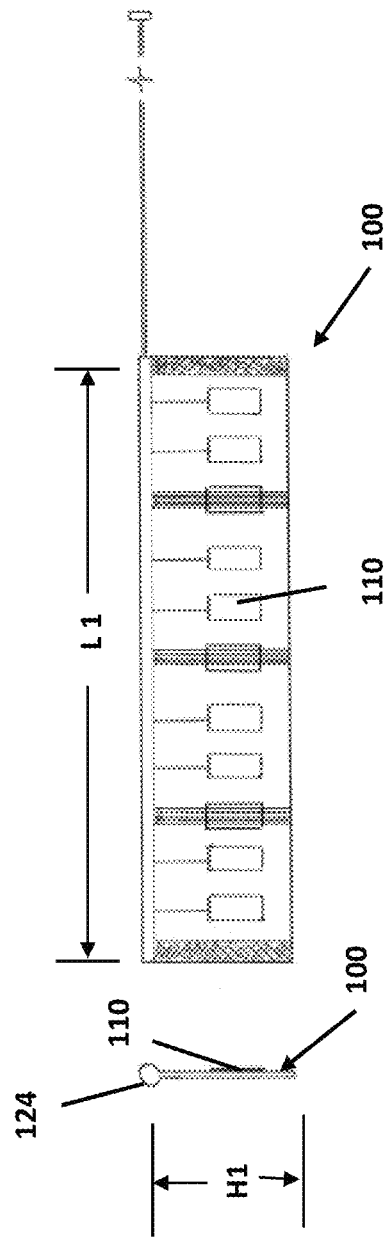
FIG. 4 is a front view of the exemplary electrode band incorporating aspects of the disclosed embodiments.

Referring also to FIGS. 3 and 4, in one embodiment, the electrode band 100 has a height H1 in the range of approximately six inches to and including seven inches. A nominal or un-stretched length L1 of the electrode band 100 can be approximately 25 inches. In alternate embodiments, the electrode band 100 will have any suitable dimensions that will enable the electrode band 100 to be expanded to encircle the patient, as is described herein.

In the example shown in FIGS. 1 and 4, the electrode band 100 is substantially rectangular in shape. In alternate embodiments, the electrode band 100 can have any suitable shape that allows the electrode band 100 to be placed around the chest of a patient, in a manner as is described herein.

In one embodiment, the side 116 of the electrode band 100 that comes in contact with the patient can have a light adhesive coating, which will aid in securing the band 100 to the patient. In the example of FIG. 1, one or more strips 114 are disposed on the side 116 of the electrode band 100. The strip 114, which extends from approximately the top side 102 of the electrode band 100 to the bottom side 104, can have a light adhesive coating disposed on the side of the strip 114 that faces and will come in contact with the patient. The strip 114 with the adhesive coating will allow the electrode band 100 to be suitably positioned and secured to the patient. The adhesive coating will be of a type that allows the electrode band 100 to be removed from the patient and repositioned if necessary. The adhesive is intended to maintain the electrode band 100 in a temporary and not permanent connection state.

As shown in the example of FIG. 1, the strip 114 is positioned between two adjacent electrodes. These strips 114 of adhesive would be approximately 4 inches wide and run from approximately the top side 102 to the bottom side 104 of the electrode band 100. In one embodiment, the adhesive strips 104 are located at suitable positions on the patient contact side 116 of the electrode band 100. Although only two strips 114 are shown in FIG. 1, the different positions of the strips 114 can include, for example, one or more of: 1) a first end 106 end of the electrode band 100, 2) the patient's right side mid-axillary line, 3) the patient's mid-back, 4) the patient's left side mid-axillary line; and 5) the second end 108 of the electrode band 100. In alternate embodiments, the electrode band 100 can include any suitable number of strips 114 disposed in any suitable position other than including the sides and back.

In one embodiment, the electrode band 100 will generally comprise an elastic type material. The use of an elastic, stretchable material, will allow the electrode band 100 to be stretched or expanded as it is placed in position around a chest of a patient. In this embodiment, a single size electrode band 100 can be manually stretched to accommodate almost all size thoraces. This provides more versatility with the electrode band 100 and reduces the need to stock different sizes.

As described above, the electrode band 100 can have a nominal length L1 or size of approximately 25 inches. When an elastic material is used, the electrode band 100 can be configured to be expanded or stretched up to a length L1 of approximately 60 inches. The nominal or un-stretched size will be a size that allows the electrode band 100 to be easily packaged, stored and carried. For example, first responders will typically carry the electrode band 100 in a medical kit or bag. A smaller nominal size will allow the electrode band 100 to be readily accommodated in such a kit or bag, where space can be at a premium, and compact packages are desirable.

The end 104 of the electrode band 100 is configured to be secured the end 106 with a closure device 108. The closure device 108 is configured to secure the ends 104, 106 together in a reliable and repeatable manner. It may be necessary to disconnect and reconnect the ends 104, 106 of the electrode band 100 during use. The closure device 108 must be capable of such connecting or coupling, disconnecting and reconnecting in a reliable and secure manner.

In the example of FIG. 1, the closure device 108 comprises Velcro®. In alternate embodiments, any suitable mechanism can be used to secure the ends 104, 106 together. For example, in one embodiment, the closure device 108 can comprise a plastic snap arrangement In one embodiment, the electrode pads 110 are embedded in the electrode band 100. For example, the electrode band 100 can comprise two layers of a material that are bonded together, referred to herein as the inner layer or side 116 and the outer layer or side 126. The inner layer or side 116 is the side of the band 100 that is configured to make contact with the patient. The electrodes 110 will be disposed between the two layers 116, 126 of the material. Generally, the electrodes 110 are secured between the two layers ors ides 116, 126 in such a manner that they are not movable within the band 100.

The inner surface or side 116 of the electrode band 100 will include openings that allow the portion or side 112 of each electrode 110 that needs to make contact with the patient to be exposed. In this manner, the electrodes 110 can be maintained in pre-determined positions and spacing in the electrode band 100. In one embodiment, the outer surface 126 may show an outline of respective electrodes 100, or some other marking.

As described above, the use of a stretchable and expandable material for the electrode band 100 enables the electrode band 100 to accommodate different chest or thorax sizes while maintaining a proper anterior/posterior alignment of electrodes 110 in each electrode pair 110A, 110B. The aspects of the disclosed embodiments advantageously maintain a correct anterior/posterior alignment of the electrodes 110 in each electrode pair 110A, 110B from the nominal or un-stretched state, to a maximum extent of the expanded or stretched state.

As noted, a typical electrode band 100 will include several pairs of embedded electrodes 110. The electrode pairs, such as 110A, 110B will be disposed in the electrode band 100 in such a way that once the electrode band 100 is applied and secured to the patient's thorax, the respective positioning of electrodes 110A, 110B in a pair is such that the electrode pairs are electrically "opposite" each other. This placement and positioning is necessary to create a desired conduction pathway through the heart or cardiac muscle of the patient during defibrillation or electric shock. As the electrode band 100 is stretched from a nominal size to a next side, the electrodes 110 will spread equally relative to one other. The pairs 110A, 110B of electrodes 110 would be electrically configured or wired in such a way that when the electrode band 100 is applied properly and electricity is discharged through any pair 110A, 110B of electrodes 110, the path of the electricity passes largely through the patient's heart.

The electrode band 100 will also include electrical wiring and wires 120 that electrically couple the electrodes 110, and the pairs 110A, 110B of electrodes. For example, a pair 110A, 110B of electrodes 110 will provide suitable "positive" and "negative" poles, as is suitable for a defibrillation event, as will be generally understood. The electrode band 100 can also include a connector 122 coupled to at least one end of the wires 120. The connector 122 can be used to connect the electrode band 100 to the defibrillator device 504, as shown in FIG. 5.

In one embodiment, the electrode band 100 can include a channel 124 through which the wires 120 can run. The wiring 120 would not be firmly secured at any location within the channel 124 and a suitable amount of wiring 120 will be provided in the channel 124 to allow the electrode band 100 to expand from the nominal state to a maximum expanded state. In this manner, the wiring 120 will not be affected by the expansion or contraction of the electrode band 100 as it is being placed on the patient. The channel 124 would be constructed in such a way, like a long pocket, as to protect the wires 120, keeping them within the channel 124 and untangled, but allowing the wires 120 to move laterally within it.

In one embodiment, the electrode band 100 can include picture diagrams and text instructions. The instructions and labels can indicate which side of the electrode band 100 should be placed against the patient's thorax and to indicate clearly where and how the band 100 should be placed on the patient. For example, the electrode band 100 could include a label indicating which side is placed against the patient's chest. The electrode band 100 can also include alignment marks, such as on the outside of the electrode band 100, the show where to align a specific reference on the electrode band 100 with an anatomical structure or other landmark of the patient.

An exemplary application of the use of the electrode band 100 is described below. In this example, the patient would need to be prepared by removing all clothing covering their torso, exposing their entire torso's skin from the abdomen to the neck. The electrode band 100 would be applied by the medical personnel or other provider, in this example, by first removing the electrode band 100 from a sealed disposable container or package. The sealed package generally ensures the sterility of the band electrode band 100 prior to use.

Once removed from the package, the medical personnel would peel off a protective disposable paper, which is adhered lightly on the patient contact side 112 of the electrode and side 116 of the electrode band 100. This will expose the conductive gel that is adhered to each electrode 110, as well the adhesive strips 114. In one embodiment, each adhesive strip can have their own, second protective, removable waxed paper strip.

Markings on the electrode band 100 can be used to indicate several locations where a particular segment of the band 100 should be positioned or laid on the patient. In one embodiment, these markings can generally coincide with the location of the adhesive strips 114 on the outside portion of the electrode band 100. This assists the medical personnel or rescuer as they are applying the electrode band 100 to stretch the electrode band 100 appropriately to fully wrap around the patient without over extending the electrode band 100. For example, there can be a line on the outside of the electrode band 100 where a segment should line up with the patient's right side mid-axillary line, mid back and left side mid-axillary line.

The rescuer would then estimate the circumference of the patient's thoracic cavity and prepare to wrap the electrode band 100 around the patient. The rescuer would then lay the beginning end of the electrode band 100, as indicated by the instructions, on the patient's mid chest at the middle of the sternum, lightly pressing the coinciding strip 114 of the electrode band 100 onto the patient's chest, allowing the adhesive to make contact and take hold. The rescuer would then begin wrapping the electrode band 100 around the side of the chest.

The rescuer, with assistance if available, would roll the patient quickly away from him and continue to wrap the electrode band 100, now peeling off the protective waxed paper covering the left mid-axillary adhesive strip 114. While keeping the electrode band 100 from twisting, the strip 114 can be pressed on, allowing the adhesive to take hold at the mid-axillary line. The rescuer would continue by stretching the electrode band 100 so the mid-back adhesive strip 114 lines up with the patient's mid-back, remove the waxed paper and press the electrode band 100 and respective strips onto the patient, allowing the mid-back adhesive strip to take hold. At this point the rescuer would push the remaining half of the electrode band 100 under the patient's side that is toward the ground.

The rescuer, with assistance if available and needed, would now reverse the roll of the patient, bringing the patient toward him. The rescuer would reach over and pull the remaining portion of the electrode band 100 (which had previously been shoved under the side of the patient), pull it out and remove the right side mid-axillary adhesive strip 114 protective waxed paper. The rescuer would then press the right side mid-axillary adhesive strip 114 to the patient's right mid-axillary line and continue to pull the electrode band 100 around the front of the patient as the rescuer rolls the patient onto their back. The rescuer finishes the application of the electrode band 100 by lining up the ends 104, 106 of the electrode band 100 and using the closure device 108 to secure the ends 106, 108 together.

The aspects of the disclosed embodiments provide a multi-axis defibrillation band. Multiple electrode and electrode pairs are arranged in the electrode band. When the electrode band is properly aligned and placed on a patient, a suitable defibrillator device can be used to provide multi-axis defibrillation. The electrode band can be configured to stretch from a nominal size to a maximum size, with any number of application positions therebetween, to accommodate any sized patient. The electrodes in the electrode band will maintain their relative placement in any size of the electrode band 100 to ensure that the electrode pairs maintain proper anterior-posterior placement to define proper electrical conduction channels during electric shock or defibrillation.

Thus, while there have been shown, described and pointed out, fundamental novel features of the invention as applied to the exemplary embodiments thereof, it will be understood that various omissions and substitutions and changes in the form and details of devices illustrated, and in their operation, may be made by those skilled in the art without departing from the spirit of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A multi-axis defibrillator electrode band for use in a multi-axis defibrillation of a person during a cardiac event, the multi-axis defibrillator electrode band comprising:
   a stretchable band, the stretchable band comprising a plurality of at least four defibrillation electrodes consecutively arranged in a spaced apart arrangement from a first end of the stretchable band to a second end of the stretchable band;
   wherein each electrode of the plurality of at least four electrodes has a pre-defined position on the stretchable band and a next electrode is disposed adjacent to a prior electrode and spaced apart from the prior electrode by a pre-determined distance;
   the plurality of at least four defibrillation electrodes defining a plurality of at least two electrode pairs, wherein a first electrode in the plurality of at least two electrode pairs is configured to be disposed on an anterior side of a chest of a subject and positioned substantially opposite a second electrode in the plurality of at least two electrode pairs configured to be disposed on a posterior side of the chest of the subject when the stretchable band is disposed in an expanded state of the stretchable band; and
   wherein in the expanded state of the stretchable band, a spacing relative to the pre-determined distance between adjacent electrodes is maintained and the positioning of the first electrode substantially opposite the second electrode in the at least two electrode pairs is maintained.

2. The multi-axis defibrillator electrode band according to claim 1, wherein the stretchable band comprises a first outer layer and a second inner layer, the plurality of defibrillation electrodes being embedded between the first outer layer and the second inner layer, the second inner layer defining a plurality of openings corresponding to respective ones of the plurality of defibrillation electrodes, a conductive surface of respective ones of the plurality of defibrillation electrodes being exposed in the openings.

3. The multi-axis defibrillator electrode band according to claim 2 wherein the first electrode and the second electrode in the plurality of at least two electrode pairs defines a conduction pathway between the first electrode and second electrode for defibrillation.

4. The multi-axis defibrillator electrode band according to claim 3 wherein the first electrode in the at least two electrode pairs configured to be in contact with an anterior surface of a thorax of a patient and the second electrode in the at least two electrode pairs configured to be in contact with a posterior surface of the thorax of the patient.

5. The multi-axis defibrillator electrode band according to claim 3, wherein the conduction pathway is maintained from an unexpanded state to the expanded state of the stretchable band.

6. The multi-axis defibrillator electrode band according to claim 1 further comprising at least one adhesive strip disposed on a surface of the stretchable band, the at least one adhesive strip configured to secure the electrode band in a usage position.

7. The multi-axis defibrillator electrode band according to claim 6, wherein the at least one adhesive strip is configured to enable the electrode band to be unsecured from the usage positioned, repositioned, and re-secured in the usage position.

8. The multi-axis defibrillator electrode band according to claim 7, wherein the at least one adhesive strip extends from approximately a top portion of the electrode band to a bottom portion of the electrode band.

9. The multi-axis defibrillator electrode band according to claim 1, wherein the stretchable band comprises an outer layer and an inner layer, the outer layer and the inner layer being joined together to form the stretchable band and wherein the inner layer defines an opening configured to hold an electrode of the plurality of at least four defibrillation electrodes.

10. The multi-axis defibrillator electrode band according to claim 9, wherein the electrode is embedded between the outer layer and the inner layer, an electrically conducting surface of the electrode being exposed by the opening.

11. The multi-axis defibrillator band according to claim 1, wherein the first electrode and the second electrode in the plurality of at least two electrode pairs defines an anterior-posterior positioning in the usage position during a defibrillation event.

12. The multi-axis defibrillator band according to claim 1, wherein the first electrode of the plurality of at least two electrode pairs defines a first conduction pole and the second electrode of the plurality of at least two electrode pairs defines a second conduction pole during a defibrillation event.

13. The multi-axis defibrillator band according to claim 1, wherein a number of electrode pairs of the at least two electrode pairs is in the range of six to ten electrode pairs.

14. The multi-axis defibrillator electrode band according to claim 1, further comprising a connecting device configured to connect a first end of the stretchable band to a second end of the stretchable band in a usage position.

15. The multi-axis defibrillator electrode band according to claim 1, wherein the at least two electrode pairs of the electrode band is configured to be placed around a chest of a person for a defibrillation event.

16. The multi-axis defibrillator electrode band according to claim 1, wherein a length of the stretchable band in an unexpanded state is approximately twenty-five inches and a length of the stretchable band in a maximum expanded state is approximately sixty inches.

* * * * *